(12) United States Patent
Binner et al.

(10) Patent No.: US 12,268,372 B2
(45) Date of Patent: Apr. 8, 2025

(54) ORAL FLUIDS COLLECTION DEVICE AND METHOD

(71) Applicant: Johnson & Johnson Consumer Inc., Skillman, NJ (US)

(72) Inventors: Curt Binner, Furlong, PA (US); Alexandru Paunescu, Clinton, NJ (US)

(73) Assignee: Kenvue Brands LLC, Summit, NJ (US)

( * ) Notice: Subject to any disclaimer, the term of this patent is extended or adjusted under 35 U.S.C. 154(b) by 818 days.

(21) Appl. No.: 17/448,904

(22) Filed: Sep. 27, 2021

(65) Prior Publication Data

US 2022/0104795 A1 Apr. 7, 2022

Related U.S. Application Data

(60) Provisional application No. 63/088,582, filed on Oct. 7, 2020.

(51) Int. Cl.
*A61B 10/00* (2006.01)

(52) U.S. Cl.
CPC ................ *A61B 10/0051* (2013.01)

(58) Field of Classification Search
CPC .... A61B 10/0051; A61B 1/24; A61J 11/0005; A61J 17/001; A61J 17/10; A61J 17/00; A61M 2202/0466; A61C 17/06
See application file for complete search history.

(56) References Cited

U.S. PATENT DOCUMENTS

| | | | |
|---|---|---|---|
| 2006/0129127 A1* | 6/2006 | Ruth | A61J 9/00 215/11.4 |
| 2012/0021375 A1* | 1/2012 | Binner | A61B 5/097 433/89 |
| 2012/0046574 A1* | 2/2012 | Skakoon | A61B 10/0051 600/576 |
| 2012/0277794 A1 | 11/2012 | Kountotsis et al. | |
| 2015/0133817 A1 | 5/2015 | Slowey et al. | |

(Continued)

FOREIGN PATENT DOCUMENTS

| | | |
|---|---|---|
| EP | 863723 B | 9/1998 |
| EP | 1397997 A | 3/2004 |

(Continued)

OTHER PUBLICATIONS

International search report and written opinion dated Dec. 22, 2021, for international application PCT/IB2021/058788.

*Primary Examiner* — Devin B Henson
*Assistant Examiner* — Jennifer Grace Baires-Tweed

(57) ABSTRACT

An oral fluids sample collection method and apparatus includes a shield having a first face and a second face; an elastomeric nipple having an outer surface and defining a nipple interior extending from the first face of the shield; and a reservoir component extending from the second face of the shield comprising a reservoir having a reservoir interior. These elements are interconnected by a plurality of fluid conduit/valve combinations, including a first combination permitting flow from the nipple interior to an atmospheric vent port disposed on an exterior surface of the oral fluids collection device; a second combination permitting flow from the reservoir interior to the nipple interior; and a third combination permitting flow from a collection port disposed on the outer surface of the nipple to an exit port in the reservoir interior.

27 Claims, 3 Drawing Sheets

(56) References Cited

U.S. PATENT DOCUMENTS

2016/0287481 A1   10/2016  Chin et al.
2018/0296196 A1   10/2018  Phillips et al.
2019/0076131 A1    3/2019  Karlsson

FOREIGN PATENT DOCUMENTS

| WO | WO 1995/030484 A | 11/1995 | |
|----|------------------|---------|--|
| WO | WO 1997/020502 A | 6/1997 | |
| WO | WO-2015116854 A1 * | 8/2015 | ......... A61B 10/0012 |
| WO | WO 2017/142463 A | 8/2017 | |

* cited by examiner

ORAL FLUIDS COLLECTION DEVICE AND METHOD

CROSS-REFERENCE TO RELATED APPLICATIONS

This application claims the benefit of U.S. provisional application 63/088,582 filed on Oct. 7, 2020, the complete disclosure of which is hereby incorporated herein by reference for all purposes.

BACKGROUND OF THE INVENTION

Field of the Invention

The present invention relates to a device and method for obtaining oral fluids samples from human subjects. More particularly, this invention relates to devices, kits and methods for obtaining saliva samples from subjects, including infants and premature infants.

Description of Related Art

Analyte testing is of human bodily fluids is routinely used to aid in the diagnosis of myriad disease states. Blood, urine, and saliva testing are quite common. The testing requires the collection of bodily fluids, followed by the analysis at the site of collection, or more commonly, at an approved testing facility.

There is an incentive to replace, where possible, invasive blood testing with non-invasive saliva testing due to convenience and cost among other benefits. Blood testing requires the invasive collection of blood, such as with a syringe. A skilled person, such as a nurse or phlebotomist, must typically be present when collecting blood. This adds both complexity and cost to the testing procedure when compared to the non-invasive collection of saliva.

In addition, a significant part of the population experience pronounced needle aversion. Infants, children and to an extent the elderly are often averse to the use of needles.

Although advancements in using saliva to diagnose many conditions previously requiring blood samples, devices designed to collect saliva samples from adults may not be usable for pediatric and neonatal patients. These patients have smaller mouths and are unable to comply with instructions. Additionally, significant safety concerns arise, as the collector must be made to prevent any possibility of detaching in the mouth and creating a choke hazard. Additionally, all parts must be designed to prevent damage to the oral cavities.

In summary, non-invasive collecting of saliva for analyte testing has advantages over complex and costly invasive blood collection. There is a need for a saliva sample collection apparatus which is safe for use, especially meeting the special needs of pediatric and neonatal patients.

BRIEF SUMMARY OF THE INVENTION

We have devised an oral fluids sample collection apparatus which is safe for use, especially meeting the special needs of pediatric and neonatal patients. The device includes a shield having a first face and a second face; an elastomeric nipple having an outer surface and defining a nipple interior extending from the first face of the shield; and a reservoir component extending from the second face of the shield comprising a reservoir having a reservoir interior. These elements are interconnected by a plurality of fluid conduit/ valve combinations, including a first fluid conduit having a first one-way valve operatively connecting and permitting flow from the nipple interior to an atmospheric vent port disposed on an exterior surface of the oral fluids collection device; a second fluid conduit having a second one-way valve operatively connecting and permitting flow from the reservoir interior to the nipple interior; and a third fluid conduit having a third one-way valve operatively connecting and permitting flow from a collection port disposed on the outer surface of the nipple to an exit port in the reservoir interior.

A method of collecting oral fluids includes:
(a) removing the oral fluids collection device described above from packaging;
(b) inserting the nipple having an initial rest volume into a subject's oral cavity;
(c) deforming the nipple to force fluid from the nipple interior to the atmospheric vent port;
(d) allowing the nipple to expand toward the initial rest volume thereby drawing fluid from the reservoir interior and decreasing fluid pressure in the reservoir component; and
(e) drawing oral fluids from the subject's oral cavity through the collection port to the reservoir interior.

Additional devices, kits, and methods are also disclosed.

DETAILED DESCRIPTION OF THE INVENTION

Figure 1:
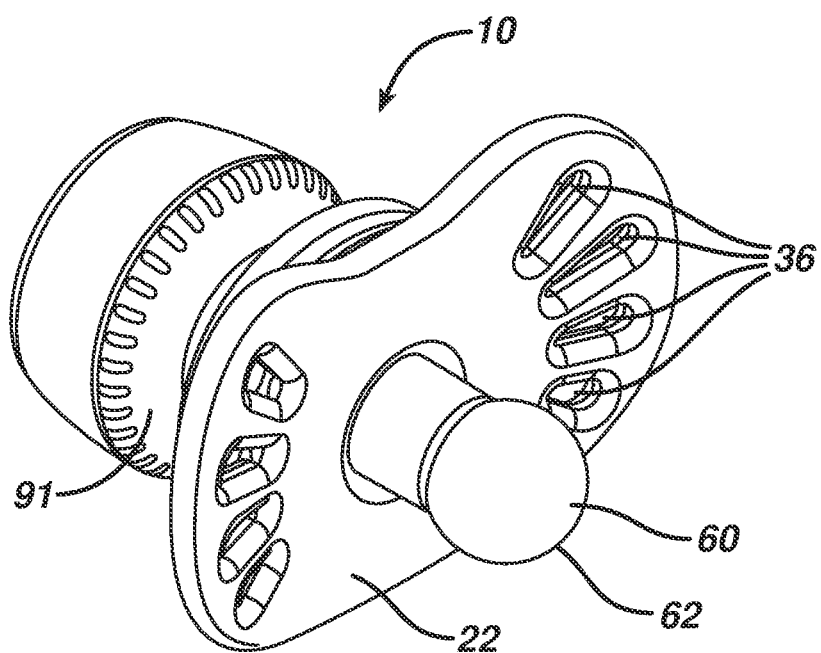
FIG. 1 is a top front perspective view of an oral fluids collection device of the present invention.

As used herein the specification and the claims, the term "oral fluids" and variants thereof relates to the bodily fluids (liquid) present in the oral cavity. Oral fluids are a mixture of saliva and "oral mucosal transudate". Saliva is produced by the salivary glands. Oral mucosal transudate enters the mouth by crossing the buccal mucosa from the capillaries.

As used herein the specification and the claims, the term "collected fluids" and variants thereof relates to oral fluids (liquids) collected by the device.

As used herein the specification and the claims, the term "elastomeric nipple" and variants thereof relates to a device nipple that has a defined shape and the ability to deform under load and return to its defined shape when the load is removed.

As used herein the specification and the claims, the term "exterior surface of the device" relates to any outwardly disposed surface of the device during use with the elastomeric nipple disposed in the subject's oral cavity.

The present invention relates to a device and method for obtaining oral fluids samples from human subjects, especially infants. The device is designed to use the non-nutritive suck (NNS) motion of the subject to create a partial vacuum in the device which draws oral care fluids from the subject's oral cavity to a reservoir within the device.

The device includes a shield, an elastomeric nipple extending from a first face of the shield, and a reservoir portion extending from the other face of the shield. The nipple and the reservoir both have a respective interior and define a respective volume. The device also has three fluid conduits each having one-way valves associated therewith. A first conduit/valve combination permits airflow from the interior of the nipple to an atmospheric vent port disposed on an exterior surface of the device. A second conduit/valve combination permits airflow from the reservoir of the device to the interior of the nipple. A third conduit/valve combination permits the flow of oral fluids from a collection port located on the nipple outer surface (disposed in the subject's oral cavity during use) to the reservoir to an exit port disposed in the reservoir.

The shield is arranged and configured to prevent the subject from attempting to take the whole device into its mouth and therefore functions to define portions of the device that can be taken into the subject's mouth from those portions of the device that remain outside of the mouth during use.

Similar to conventional pacifiers, the shield has a primary planar orientation that, in use, is disposed substantially parallel to the subject's lips. The shield optionally includes a plurality of ventilation holes through its thickness that can permit air to pass through if the subject breathes through its mouth or to provide other aesthetic or functional benefits.

The material used in making the shield is not critical and may include conventional pacifier shield materials, such as non-toxic plastic materials. Exemplary plastics include, without limitation, polyethylene terephthalate (PET), high density polyethylene (HDPE), low density polyethylene (LDPE), or polypropylene (PP).

The shield may be formed by any useful plastic formation processes including, without limitation, injection molding, thermoforming, and the like.

The elastomeric nipple extends from one face of the shield in a direction substantially perpendicular to the primary planar orientation of the shield. The elastomeric nipple has a nipple outer surface and an aperture formed in the nipple outer surface. As indicated above, the elastomeric nipple also defines a nipple interior. The nipple interior is hollow, a void capable of accepting fluids.

The material used in making the elastomeric nipple is not critical and may include conventional pacifier elastomeric nipple materials, such as non-toxic elastomeric materials. However, it is desirable to control the stiffness of the elastomeric nipple produced therefrom to enable the nipple to deform as described with more detail, below. Exemplary elastomeric materials include, without limitation, rubber (natural or latex), silicones, or soft plastics. Rubbers, silicones, and soft plastics are readily deformable, and they are therefore, effective when deformed by the non-nutritive sucking motion (NNS) when elastomeric nipple is in the subject's mouth. In non-nutritive sucking, the subject's tongue generally travels in characteristic peristaltic motion (e.g., a left to right wave-like motion).

The elastomeric nipple may be formed by any useful plastic formation processes including, without limitation, injection molding, thermoforming, liquid silicone injection molding, and the like.

It may be desirable to select the same material for both the shield and nipple. This can be useful to integrate these components and eliminate a secondary connection of the two parts which otherwise could be a failure point. In such a construction, the material of both the shield and nipple may be a silicone or a soft plastic including, without limitation, thermoplastic elastomers, or low durometer polyurethanes, and the like.

The elastomeric nipple may be connected to the shield through many methods that may vary depending on the materials used for the two elements. Useful methods include, without limitation, mechanical interference fit, fasteners/clamps, bonding (e.g., adhesive, solvent, and/or thermal including ultrasonic). Of course, if the elastomeric nipple and shield are made of the same material, they can be formed together in a single operation. Alternatively, the shield and elastomeric nipple can be injection molded over a stiffening element to provide appropriate rigidity to the shield.

A reservoir is associated with the second face of the shield and is disposed outside of the subject's mouth during use. As indicated above, the reservoir defines a reservoir interior, a void capable of accepting fluids, wherein oral fluids, such as saliva, that are collected by device are stored.

The reservoir may also have at least one deformable zone that may be one or more walls or portions thereof. The reservoir interior under ambient conditions defines an initial reservoir interior with the at least one deformable zone in a rest condition. As described below regarding the operation of the device, the at least one deformable zone is capable of elastic deformation to permit the reservoir volume to decrease below the initial volume when certain operating conditions are present and to return to its rest condition under normal operating conditions return.

The reservoir may also contain a non-toxic stabilization buffer solution. The presence of the stabilization buffer preserves the collected fluids for analysis for days, or even weeks, after collection. The buffer solution may be disposed within the reservoir interior or added to the reservoir interior.

Because oral fluids, such as saliva, contain proteins and other biological materials which may adhere to the interior walls of the reservoir, these interior walls may be coated with substances preventing these proteins and other biological materials from adhesion thereto.

In order to be tested, the oral fluids collected by the device must be transferred from the device to a testing facility. The testing facility may be part of an at-home testing system or it may be at a remote location. Therefore, the test fluid must be extracted from the device. This may be done by removing the reservoir from the device and transporting it to the test facility, especially if the facility is at a remote location. One convenient container useful for transporting the collected fluids is the reservoir itself. Alternatively, the collected fluids may be transferred from the reservoir to a transportation vial. Ultimately, the collected fluids can be removed from the transport container via syringe or other useful transfer means.

The reservoir may be included in a reservoir component that is arranged and configured for demountable engagement to the shield.

In addition to providing for the collection of oral fluids, the reservoir also functions as a liquid/gas separator. As described in more detail, below, the reservoir holds the oral fluids collected by the device and separates the oral fluids flow stream from the air (gas) stream through the device.

To assist in the liquid/gas separation, the reservoir may incorporate a dam to restrict movement of the collected fluids to the second conduit/valve combination, described below.

The material used in making the reservoir is not critical and may include conventional materials, such as non-toxic plastic materials. Exemplary plastics include, without limitation, Polyethylene Terephthalate (PET), High Density Polyethylene (HDPE), Low Density Polyethylene (LDPE), Polypropylene (PP), or Polyurethane.

The reservoir may be formed by any useful plastic formation processes including, without limitation, injection molding, thermoforming, and the like. Reservoir can also be manufactured by standard plastic manufacturing techniques such as injection molding. The at least one deformable zone may be comprised of elastomeric materials such as rubbers, silicones, and soft plastics including without limitation, thermoplastic elastomers, or low durometer polyurethanes.

The first conduit/valve combination permits airflow from the interior of the nipple to an atmospheric vent port disposed on an exterior surface of the device. Depending on the specific details and arrangement of the device, the atmospheric vent port may be disposed on the shield or on an optional housing for the reservoir. The location of the one-way valve along the first conduit path is not critical. It may be located to enhance effective sanitization of the device.

The second conduit/valve combination permits airflow from the reservoir of the device to the interior of the nipple. Again, the location of the one-way valve along the second conduit path is not critical. It may be located to enhance effective sanitization of the device.

The second conduit opening is disposed in the reservoir walls in a location designed to minimize its exposure to collected fluids.

The third conduit/valve combination permits the flow of oral fluids from a collection port located on the nipple outer surface (disposed in the subject's oral cavity during use) to the reservoir to an exit port disposed in the reservoir.

The exit port may be disposed in a central portion of reservoir interior to provide an air gap between the exit port and the liquid surface of the previously collected oral fluids in the reservoir. Thus, previously collected oral fluids does not block the flow of new oral fluids insults from exit port.

As will be described, below, in reference to the drawing, the exit port of the third conduit is disposed in a central portion of the reservoir interior to provide the air gap between the exit port and any previously collected oral fluids.

The oral fluids collection device generally described above collects and captures oral fluids such as saliva and oral mucosal transudate. Gases in the oral cavity may also be collected, but the fluid conduit/valve elements in device generally allow a substantial volume of these gases to pass through the system via the atmospheric vent port, while only oral fluids remain in the reservoir interior.

The oral fluids collection device generally described above may be manufactured, packaged, and sold as a unitary disposable device. Packaging protects oral fluids collection device from contamination from damage as it keeps the device and/or its components secure as it is shipped from the manufacturer to the consumer.

However, a preferred system is a kit of a durable portion and a plurality of individually packaged reservoir portions. In this kit, the durable portion includes the shield and elastomeric nipple (and associated conduit/valve elements), and the individually packaged reservoir portions include the reservoir and any an optional housing to enclose the reservoir (and associated conduit/valve elements). Thus, a reservoir portion is removed from its packaging and assembled with the durable portion for use. Alternately, one device may be packaged in a fully assembled condition with additional, separately packaged reservoir portions. After use, the reservoir portion is disassembled from the durable portion, and the collected fluids are subsequently transported for analysis.

The reservoir portion is arranged and configured for demountable engagement to the durable portion. Thus, a first reservoir portion can be engaged to the durable portion for a first sampling of the subject and demounted from the durable portion. The durable portion can be appropriately cleaned and/or sanitized, and a second reservoir portion can be unpackaged and engaged to the durable portion for a second sampling of the subject—or even a sampling of a second subject. Examples of engagements useful in such demountable engagement include, without limitation, screw, pin, bayonet, hook, and clamp.

Optionally, the skin and oral cavity-contacting elements could be disposable, including perhaps the elastomeric nipple and a shield liner disposed toward the lips during use and possibly even the reservoir and conduits. While a structural shield component and reservoir housing could be reusable (durable). This could permit additional components to be incorporated into the durable components.

Refill packages, containing a plurality of packaged reservoir portions and non-durable portions, may also be provided to consumers.

The oral fluids collection kit made available to consumers may also include one or more containers or packages for sending reservoirs to a test facility (testing laboratories, hospitals, clinics, medical testing facilities) for analysis. The oral fluids collection kit may also have directions to transport the reservoir portion to a test facility. Thus, reservoir portion may be sealed and placed in package supplied to consumer in the kit for shipping through the mail or delivery service. The supplied package may be pre-addressed and may also be insulated to protect the oral collected fluids from temperature extremes which might affect oral fluids analysis. The return package supplied may optionally incorporate a sensor which can be used by the testing laboratory to verify that reservoir was not exposed to temperature extremes.

The oral fluids collection device generally described above is used in a method of collecting oral fluids. At an initial point, the pressure in nipple interior, reservoir interior, and the subject's oral cavity, or mouth, are equal.

If oral fluids collection device is disposed in packaging, the oral fluids collection device and/or its components are removed from packaging (and assembled, if necessary). As with traditional pacifiers, the elastomeric nipple is inserted into the subject's oral cavity. The non-nutritive sucking (NNS) motion of the subject on the elastomeric nipple results in the deformation (collapsing) of elastomeric nipple. Deforming the elastomeric nipple forces fluid, or air, from nipple interior to atmospheric vent port, where it is expelled to the atmosphere. The path followed by the fluid is from nipple interior, into first fluid conduit and associated first one-way valve, and finally exiting oral fluids collection device through atmospheric vent port disposed on an exterior surface of the device. First one-way valve prevents air from outside of oral fluids collection device backfilling nipple interior via atmospheric vent port.

Next, the deformed elastomeric nipple is allowed to expand to its original shape. In non-nutritive sucking, the infant's tongue travels in peristaltic motion which alternately adds and then removes a load on elastomeric nipple. As elastomeric nipple re-expands, the pressure in nipple interior decreases. To re-equilibrate the pressure between nipple interior and reservoir interior, gas must flow from reservoir interior, to nipple interior. The path followed by the gas is from reservoir interior, into second fluid conduit and associated second one-way valve, and finally into nipple interior.

Since gas has been removed from the interiors of oral fluids collection device, the pressure in nipple interior and reservoir interior are lower than the pressure in the subject's oral cavity. To rebalance the fluid pressure between reservoir interior and the subject's oral cavity, fluid, or air, must return to reservoir interior. The source of the fluid is the subject's oral cavity. Oral fluids, or saliva, is drawn from the subject's oral cavity to reservoir interior. The path followed by the oral fluids is from the oral cavity, through collection port located on nipple outer surface, into third fluid conduit, through third one-way valve, and finally into reservoir interior.

Again, the reservoir may also have at least one deformable zone, that zone deforms, decreasing the volume of reservoir interior. When at least one deformable zone returns to its rest condition, a pressure differential between the oral cavity and reservoir interior forms. As discussed above, to rebalance the fluid pressure in reservoir interior and the subject's oral cavity, fluid flows from subject's oral cavity to reservoir interior as discussed above.

In addition, the at least one deformable zone in the reservoir allows for the accumulation of moderate vacuum (negative pressure) in the reservoir, especially if the collection port is blocked by the subject's tongue, successive suckling cycles still move gas out of elastomeric nipple. The at least one deformable zone deforms more with each cycle and accumulates the mechanical stress in the at least one deformable zone that can then provide the increased negative pressure when collection port is unblocked and the at least one deformable zone returns to its rest condition.

Analyzing the oral fluids collected by oral fluids collection device may be performed at the site of collection, such as in-home test kits, or at numerous testing laboratories located at hospitals, clinics and medical testing facilities.

When analysis is performed at testing laboratories outside the home, the collected fluids must be shipped to the testing site. Therefore, the device containing the collected fluids may be shipped in its entirety to the testing site. Alternatively, the reservoir portion may be separated from the durable portion.

To perform the analysis of oral fluids, they must be removed from reservoir. The collected fluids may be removed from reservoir by syringe, either by puncturing a reservoir that has been sealed for shipment, or through an opening in the reservoir created when removing a reservoir portion from a durable portion.

The presently disclosed subject matter will now be described more fully hereinafter with reference to the accompanying drawings and examples that are provided so this disclosure will be thorough and complete. Unless otherwise defined, all technical and scientific terms used herein have the same meaning as commonly understood by one of ordinary skill in the art to which this presently described subject matter belongs.

Figure 2:
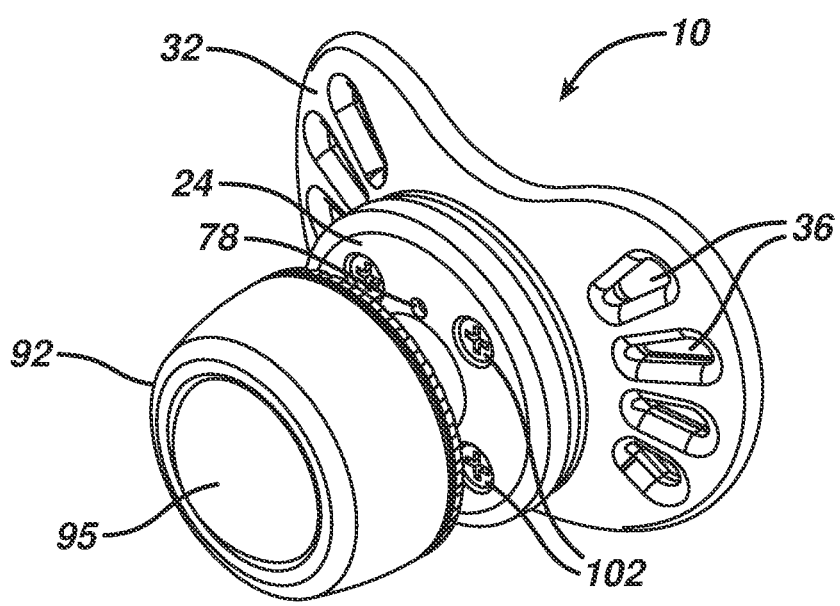
FIG. 2 is a top back perspective view of the oral fluids collection device of FIG. 1.
Figure 3:
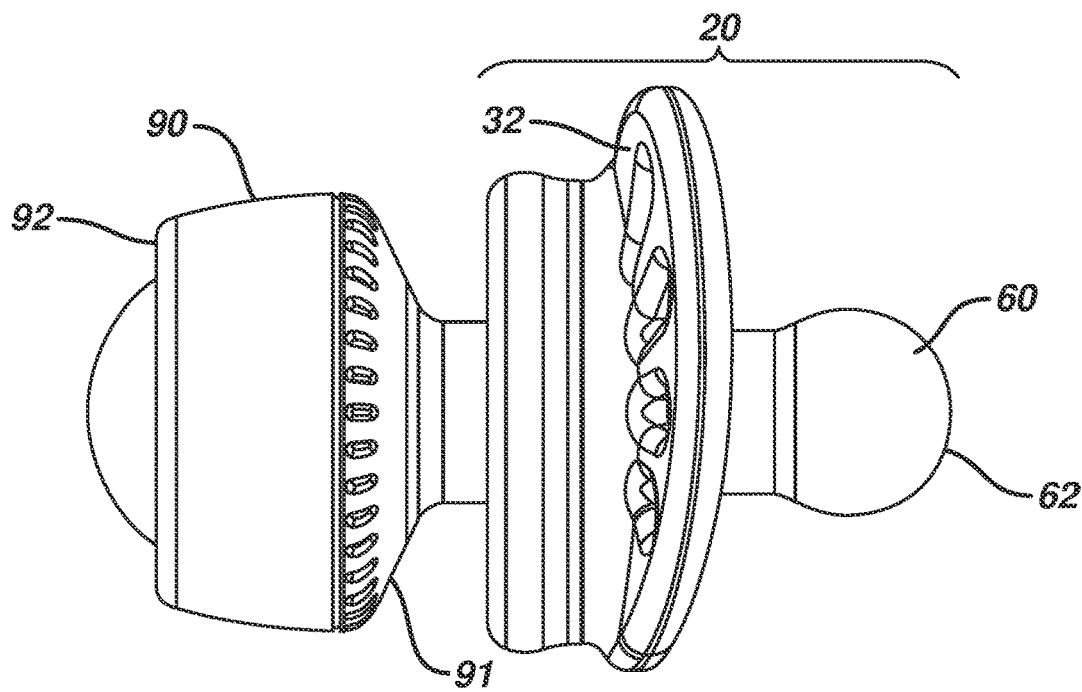
FIG. 3 is a side view of the oral fluids collection device of FIG. 1.
Figure 4:
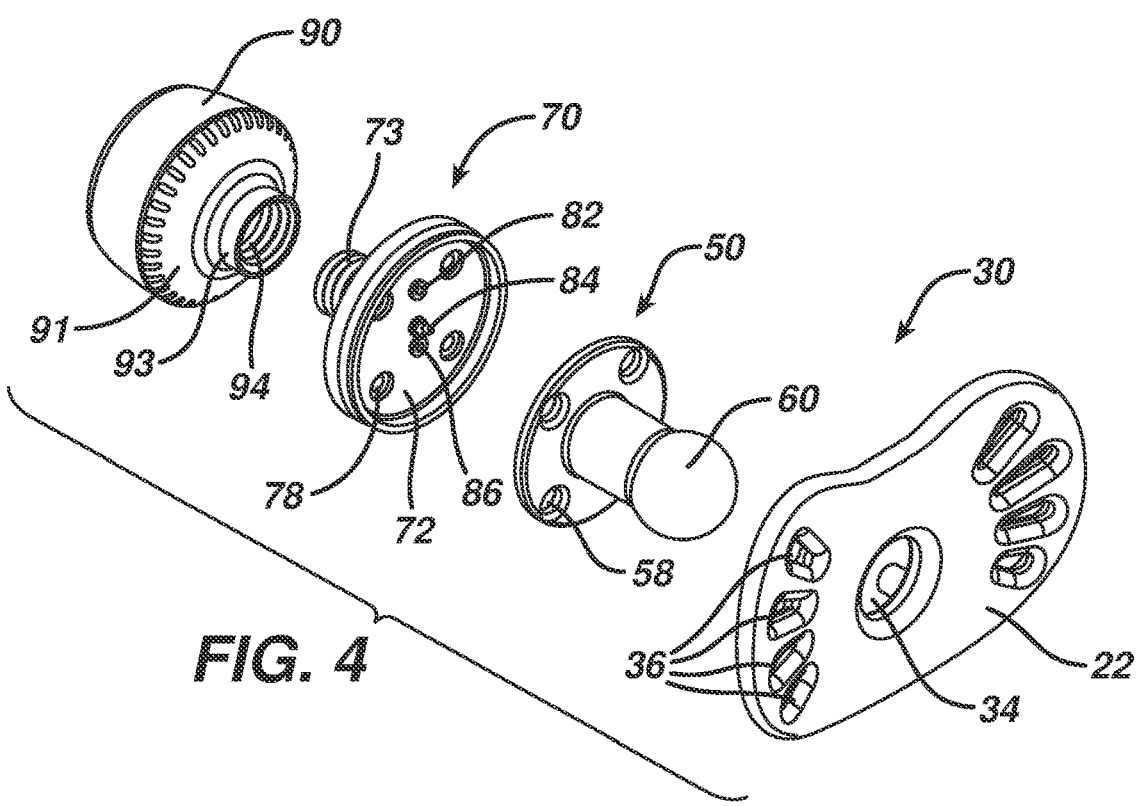
FIG. 4 is a top front exploded perspective view of the oral fluids collection device of FIG. 1.
Figure 5:
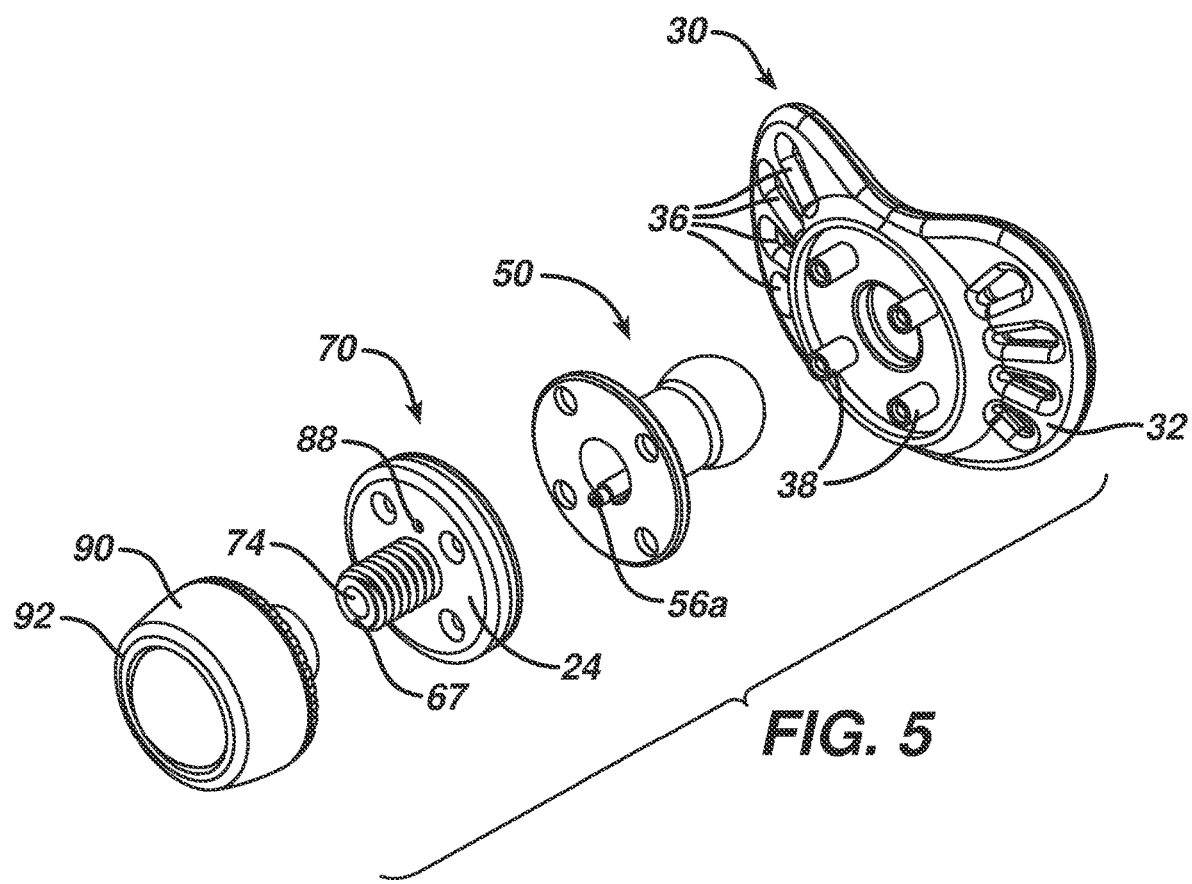
FIG. 5 is a top back exploded perspective view of the oral fluids collection device of FIG. 1.
Figure 6:
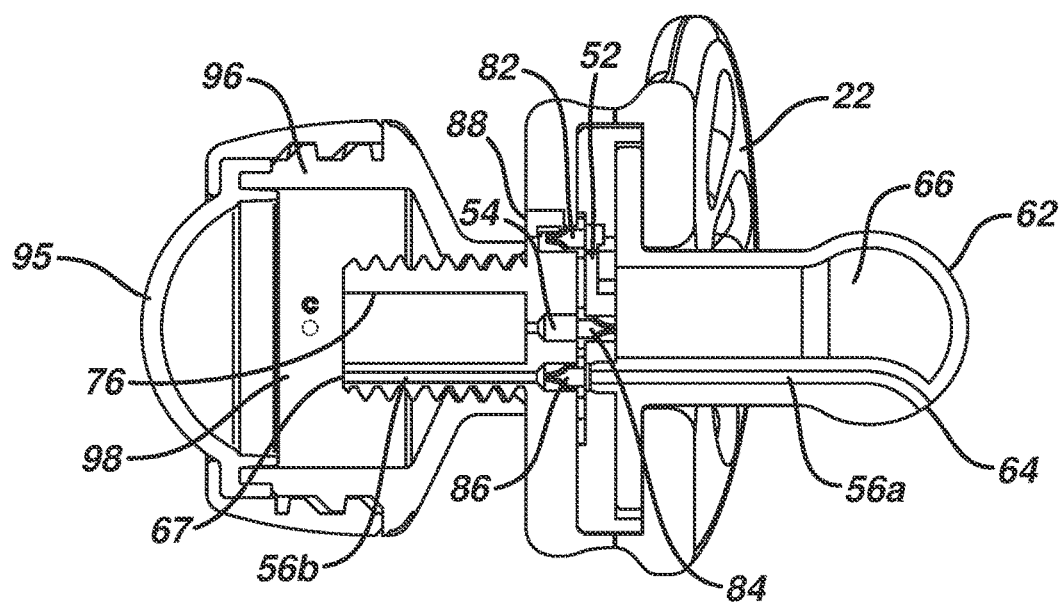
FIG. 6 is a partial cross-sectional side view of the oral fluids collection device of FIG. 1.

Referring now to the drawings wherein like reference numerals designate corresponding parts throughout the several views, FIGS. 1 to 6 are views of an oral fluids collection device of the present invention. FIGS. 1 and 2 are a top front and back, respectively, perspective views of an oral fluids collection device 10. FIG. 3 is a side view of device 10. FIGS. 4 and 5 are top front and back, respectively, exploded perspective views device 10. Finally, FIG. 6 is a partial cross-sectional side view of oral fluids collection device 10.

In FIG. 1, elastomeric nipple 60 is shown extending from first face 22 of the shield 30. FIG. 2 shows reservoir component 90 extending from second face 24 of first component 20.

FIG. 3, a side view of oral fluids collection device 10, shows a device 10 having two parts, a first component 20 and a reservoir component 90. FIGS. 4 and 5 show first component 20 as having three elements: a shield 30, a nipple element 50, and a clamp 70. As will be described later, the three elements can be assembled to form first component 20.

Shield 30 has a first face 22, a second face 32 opposite thereof. The shield 30 also has an aperture 34, ventilation holes 36, and aligner pins 38.

Nipple element 50 has an elastomeric nipple 60 and aligner guide holes 58. Elastomeric nipple 60 has a nipple outer surface 62 directed to the subject's mouth and a nipple interior 66.

Clamp 70 has a first face 72, a second face 24, a second fluid conduit 54, an exit port 67, a connector 73, an aperture 74, aligner guide holes 78, a first one-way valve 82, a second one-way valve 84, a third one-way valve 86, and an atmospheric vent port 88. Connector 73 is shown extending from second face 24 of clamp 70 and having aperture 74 and exit port 67. First one-way valve 82, second one-way valve 84, and third one-way valve 86 are disposed at the surface of first face 72 of clamp 70. Atmospheric vent port 88 is disposed at the surface of second face 24 of clamp 70 and is exposed to the atmosphere. Although atmospheric vent port 88 is disposed at the surface of second face 24 of clamp 70, it may be located on any exterior surface of oral fluids collection device 10.

When oral fluids collection device 10 is assembled, three fluid conduits are formed. These fluid conduits carry fluids between the components and are shown in FIG. 6. First fluid conduit 52 which runs from nipple interior 66 to first one-way valve 82 is formed when nipple element 50 and clamp 70 are connected. First fluid conduit 52 and first one-way valve 82 operatively connect and permit the flow of fluid from nipple interior 66 to atmospheric vent port 88.

A second fluid conduit 54 runs from reservoir interior 98 to second one-way valve 84. Second fluid conduit 54 and second one-way valve 84 operatively connect and permit the flow of fluid from reservoir interior 98 to nipple interior 66.

Nipple element 50 also has first portion of third fluid conduit 56*a*, while clamp 70 has second portion of third fluid conduit 56*b*. When oral fluids collection device 10 is assembled, third fluid conduit is formed, and carries oral fluids from the oral cavity of the subject to reservoir component 90 of oral fluids collection device 10.

Shield 30 and clamp 70 may be composed infant safe materials such as plastics.

Nipple element 50 may be composed of infant safe materials such as rubber (natural or latex), silicones, or soft plastics.

Shield 30, nipple element 50 and clamp 70 may be manufactured by standard plastic manufacturing techniques such as injection molding.

First component 20 of oral fluids collection device 10 is assembled as follows. Nipple element 50 is aligned with shield 30 so that elastomeric nipple 60 of nipple element 50 passes through aperture 34 of shield 30 and aligner pins 38 of shield 30 pass through aligner guide holes 58 of nipple element 50. Elastomeric nipple 60 now extends from first face 22 of shield 30, and therefore, extends from the first face 22 of first component 20.

Clamp 70 is aligned with nipple element 50 so that aligner guide holes 78 of clamp 70 is aligned with aligner pins 38 of shield 30.

Shield 30, nipple element 50 and clamp 70 are held together by fasteners 102. Aligner pins 38 of shield 30 have inner female threads, and fasteners 102 are screw fasteners. Other types of fasteners include bolts and pins. Alternatively, the three elements of first component 20 of oral fluids collection device 10 may be bonded together using glue, heat sealing, etc.

The figures also show reservoir component 90 of oral fluids collection device 10. Reservoir component 90 has a proximal end 91, a distal end 92, a side wall 96, and a connector 93 with an aperture 94. Connector 93 extends from proximal end 91 of reservoir component 90. Rear cover 95 is disposed at distal end 92 of reservoir component 90. Reservoir component 90 also has a reservoir interior 98, which is a void volume in which oral fluids such as saliva captured by oral fluids collection device 10 are stored.

Reservoir component 90 can also be manufactured by standard plastic manufacturing techniques such as injection molding. Rear cover 95 may be comprised of elastomeric materials such as rubbers, silicones, and soft plastics, resulting in reservoir component 90 having at least one deformable zone.

To finish the assembly of oral fluids collection device 10, first component 20 and reservoir component 90 are attached so that reservoir component 90 extends from second face 24 of shield 30. The outward surface of connector 73 of clamp 70 is male threaded, while the inward surface of aperture 94 on reservoir component 90 is female threaded. So, first component 20 and reservoir component 90 are screwed together to completed assembly of oral fluids collection device 10. Alternatively, outward surface of connector 73 of clamp 70 may be female threaded, while the inward surface of aperture 94 on reservoir component 90 may be male threaded. Alternatively, first component 20 and reservoir component 90 are snapped together, or there is a resistance fit, or a bayonet fit between connector 73 and aperture 94.

FIG. 6 is a partial cross-sectional side view of oral fluids collection device 10. As previously discussed, first fluid conduit 52 runs from nipple interior 66 to first one-way valve 82. First fluid conduit 52 and first one-way valve 82 operatively connect and permit the flow of fluid from nipple interior 66 to atmospheric vent port 88.

Second fluid conduit 54 runs from reservoir interior 98 to second one-way valve 84. Second fluid conduit 54 and second one-way valve 84 operatively connect and permit the flow of fluid from reservoir interior 98 to nipple interior 66.

Third fluid conduit, comprising first portion of third fluid conduit 56a and second portion of third fluid conduit 56b runs from collection port 64 located on nipple outer surface 62 through third one-way valve 86, and connector 73. Third one-way valve 86 is operatively connected to first portion of third fluid conduit 56a and second portion of third fluid conduit 56b, and it permits the flow of fluid from collection port 64 to reservoir interior 98 through exit port 67.

Exit port 67 is disposed in a central portion of reservoir interior 98. In FIG. 6, the dotted circle labeled "c" is a linear distance from proximal end 91, distal end 92, and side wall 96 of reservoir component 90. Dotted circle "c" is defined as 75 percent of the linear distance from any point on proximal end 91, distal end 92, and side wall 96. In this work, central portion of reservoir interior 98 is defined as any location inside reservoir interior 98 which is greater than 25 percent of the linear distance from any point on proximal end 91, distal end 92 and side wall 96 of reservoir component 90 to circle "c".

For example, in FIG. 6, exit port 67 is disposed greater than approximately 75 percent of the linear distance from any point on proximal end 91 to circle "c", greater than approximately 100 percent of the linear distance from any point on distal end 92 to circle "c", greater than approximately 60 percent of the linear distance from any point on side wall 96 to circle "c". Therefore, exit port 67 is defined as disposed in a central portion of reservoir interior 98.

The advantage of having exit port 67 disposed in a central portion of reservoir interior 98 is that oral fluids collected in reservoir interior 98 is not blocking newer fluids from flowing out of exit port 67.

In addition, connector 73 and its associated aperture 74 project into reservoir interior 98 and form a dam 76. Dam 76 provides a liquid/gas separation barrier to prevent collected fluids in reservoir interior 98 from contacting second one-way valve 84 and flowing from reservoir interior 98 to nipple interior 66. Oral fluids in nipple interior 66 may affect the ability of oral fluids collection device 10 to collecting additional oral. The central location of aperture 74 is in reservoir interior 98 also allows the pacifier to operate in most orientations.

The oral fluids collection device 10 described with reference to the figures can be used in a method of collecting oral fluids for analysis. The method is generally described above. The following illustrates how the device shown in the figures can be used in this general method.

At an initial point, the pressure in nipple interior 66, reservoir interior 98, and the subject's (infant's) oral cavity, or mouth, are equal.

If oral fluids collection device 10 is disposed in packaging, the consumer first removes oral fluids collection device 10 from the packaging. Elastomeric nipple 60 is inserted into the subject's oral cavity. The non-nutritive sucking (NNS) motion of the subject on the elastomeric nipple 60 results in the deformation (collapsing) of elastomeric nipple 60. Deforming the elastomeric nipple 60 forces fluid, or air, from nipple interior 66 to atmospheric vent port 88, where it is expelled to the atmosphere. The path followed by the fluid is from nipple interior 66, into first fluid conduit 52, through first one-way valve 82, and finally exiting oral fluids collection device 10 through atmospheric vent port 88. First one-way valve 82 prevents air from outside of oral fluids collection device 10 backfilling nipple interior 66 via atmospheric vent port 88.

Next, the deformed elastomeric nipple 60 is allowed to expand to its original shape. In non-nutritive sucking, the infant's tongue travels in peristaltic motion which alternately adds and then removes a load on elastomeric nipple 60. As elastomeric nipple 60 re-expands, the pressure in nipple interior 66 decreases. To re-equilibrate the pressure between nipple interior 66 and reservoir interior 98, gas must flow from reservoir interior 98, to nipple interior 66. The path followed by the gas is from reservoir interior 98, into second fluid conduit 54, through second one-way valve 84, and finally into nipple interior 66.

Since gas has been removed from the nipple interior 66 and reservoir interior 98 of oral fluids collection device 10, the pressure in nipple interior 66 and reservoir interior 98 are lower than the pressure in the subject's oral cavity. Now, to rebalance the fluid pressure between reservoir interior 98 and the subject's oral cavity, fluid, or air, must return to reservoir interior 98. The source of the fluids is the subject's oral cavity. Oral fluids, or saliva, is drawn from the subject's oral cavity to reservoir interior 98. The path followed by the oral fluids is from the oral cavity, through collection port 64 located on nipple outer surface 62, into third fluid conduit (56a and 56b) through third one-way valve 86, and finally into reservoir interior 98.

As mentioned earlier, reservoir interior 98 is where oral fluids such as saliva captured by oral fluids collection device 10 is stored. The collected fluids may now be analyzed to aid in the diagnosis of disease states in the body.

When analysis is performed at testing laboratories outside the home, the saliva must be shipped to the testing site. After collection of oral fluids by oral fluids collection device 10, the device may be shipped in its entirety to the testing site. Alternatively, after collection of oral fluids by oral fluids collection device 10, first component 20 and reservoir component 90 may first be separated by removing reservoir component 90 from first component 20. Outward surface of connector 73 of clamp 70 is male threaded, while the inward surface of aperture 94 on reservoir component 90 is female threaded. So, first component 20 and reservoir component 90 are screwed together to completed assembly of oral fluids collection device 10. Unscrewing first component 20 and reservoir component 90 is a means of separating the parts of oral fluids collection device 10.

To perform the analysis of oral fluids, the fluids must be removed from reservoir component 90. In some embodiments, the oral fluids being tested is removed from reservoir component 90 of oral fluids collection device 10 by puncturing the reservoir component 90 using a syringe. Therefore, first component 20 and reservoir component 90 may be separated by unscrewing, and a syringe used to remove the collected fluids.

If the reservoir component 90 of the oral fluids collection kit is intended to be sent to a testing laboratory (hospitals, clinics, medical testing facilities) for analysis, the reservoir component 90 and first component 20 are separated when sufficient oral fluids is collected in reservoir component 90. Reservoir component 90 may be sealed by disposing a sealing means upon aperture 94. As shown in FIG. 4, the inner surface of aperture 94 on reservoir component 90 is female threaded. So, a plug with external male threads may be used to seal reservoir component 90. Reservoir component 90 may be disposed in kit supplied package for shipping through the mail or delivery surface. The supplied package may be pre-addressed and may also be insulated to protect the oral fluids collected in reservoir component 90 from temperature extremes which might affect oral fluids analysis.

EXAMPLE

A sample oral fluids collection device 10 was manufactured to test the design. Conventional rapid prototyping technologies were used to form the shield 30, clamp 70, and reservoir component 90. All were manufactured on an Objet Polyjet rapid prototyping machine (Stratasys Gmbh, Rheinmunster, DE) using a rigid opaque polyjet photopolymer sold under the tradename VeroWhitePlus RGD835 (Stratasys Gmbh, Rheinmunster, DE). The elastomeric components (elastomeric nipple 60 is shown and rear cover 95) were molded using prototype molds and silicone casting resin sold under the tradename DragonSkin™ 30 (Smooth-On, Inc., Macungie, PA). First one-way valve 82, second one-way valve 84, and third one-way valve 86 were supplied by Minivalve, Inc. (Cleveland, OH). These components were assembled using four standard stainless-steel screws. Once assembled, the device was tested for fluids handling ability by submerging collection port 64 in a beaker of water, then applying successive compressive forces to elastomer nipple 60. It was observed that with successive compressions on elastomer nipple 60, fluid flow was generated and reservoir component 90 accumulated the fluids.

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

The invention claimed is:

1. An oral fluids collection device comprising:
   (a) a shield having a first face and a second face;
   (b) an elastomeric nipple having an outer surface and defining a nipple interior extending from the first face of the shield;
   (c) a reservoir component extending from the second face of the shield comprising a reservoir having a reservoir interior;
   (d) a first fluid conduit having a first one-way valve operatively connecting and permitting flow from the nipple interior to an atmospheric vent port disposed on an exterior surface of the oral fluids collection device;
   (e) a second fluid conduit having a second one-way valve operatively connecting and permitting flow from the reservoir interior to the nipple interior; and
   (f) a third fluid conduit having a third one-way valve operatively connecting and permitting flow from a collection port disposed on the outer surface of the nipple to an exit port in the reservoir interior.

2. The oral fluids collection device of claim 1 wherein the reservoir component is arranged and configured for demountable engagement to the shield.

3. The oral fluids collection device of claim 1 wherein the reservoir component further comprises at least one deformable zone.

4. The oral fluids collection device of claim 1 wherein the reservoir component further comprises a housing to enclose the reservoir.

5. The oral fluids collection device of claim 1 wherein the reservoir component has disposed within the reservoir interior a buffer solution.

6. The oral fluids collection device of claim 1 wherein the exit port is arranged and configured to provide an air gap between liquids in the exit port and liquids in the reservoir interior.

7. A method of collecting oral fluids comprising:
   (a) removing the oral fluids collection device of claim 1 from packaging;
   (b) inserting the nipple having an initial rest volume into a subject's oral cavity;
   (c) deforming the nipple to force fluid from the nipple interior to the atmospheric vent port;
   (d) allowing the nipple to expand toward the initial rest volume thereby drawing fluid from the reservoir interior and decreasing fluid pressure in the reservoir component; and
   (e) drawing the oral fluids from the subject's oral cavity through the collection port to the reservoir interior.

8. The method of claim 7 wherein the oral fluids comprise saliva.

9. The method of claim 7 further comprising demounting the reservoir component from the shield.

10. The method of claim 9 further comprising adding a buffer solution to the reservoir interior.

11. The method of claim 10 further comprising analyzing the oral fluids.

12. The method of claim 7 wherein the reservoir component has disposed within the reservoir interior a buffer solution.

13. The method claim 12 further comprising analyzing the oral fluids.

14. An oral fluids collection kit comprising:
  (a) a durable component comprising:
    (i) a shield having a first face and a second face; and
    (ii) an elastomeric nipple having an outer surface and defining a nipple interior extending from the first face of the shield; and
  (b) a plurality of attachable reservoir components arranged and configured for demountable engagement to the shield, each attachable reservoir component comprising a reservoir having a reservoir interior;
  wherein an assembly of one of the plurality of attachable reservoir components to the durable component defines an oral fluids collection device having (1) a first fluid conduit having a first one-way valve operatively connecting and permitting flow from the nipple interior to an atmospheric vent port disposed on an exterior surface of the oral fluids collection device; (2) a second fluid conduit having a second one-way valve operatively connecting and permitting flow from the reservoir interior to the nipple interior; and (3) a third fluid conduit having a third one-way valve operatively connecting and permitting flow from a collection port disposed on the outer surface of the nipple to the reservoir interior.

15. The oral fluids collection kit of claim 14 wherein each of the plurality of attachable reservoir components is individually packaged.

16. The oral fluids collection kit of claim 14 wherein each of the plurality of attachable reservoir components further comprises at least one deformable zone.

17. The oral fluids collection kit of claim 14 wherein each of the plurality of attachable reservoir components further comprises a housing to enclose the reservoir.

18. The oral fluids collection kit of claim 14 wherein the reservoir component each of the plurality of attachable reservoir components has disposed within the reservoir interior a buffer solution.

19. The oral fluids collection kit of claim 14 wherein the exit port is disposed in a central portion of the reservoir interior of each of the plurality of attachable reservoir components.

20. The oral fluids collection kit of claim 14 further comprising directions to transport a used reservoir portion of the plurality of reservoir components to a test facility.

21. A method of collecting oral fluids using the oral fluids collection kit of claim 14 comprising:
  (a) removing one of the plurality of attachable reservoir components of the oral fluids collection kit of claim 14 from packaging;
  (b) attaching the attachable reservoir component of step (a) to the durable component to form the oral fluids collection device;
  (c) inserting the nipple having an initial rest volume into a subject's oral cavity;
  (d) deforming the nipple to force fluid from the nipple interior to the atmospheric vent port;
  (e) allowing the nipple to expand toward the initial rest volume thereby drawing fluid from the reservoir interior and decreasing fluid pressure in the reservoir component; and
  (f) drawing the oral fluids from the subject's oral cavity through the collection port to the reservoir interior.

22. The method of claim 21 wherein the oral fluids comprise saliva.

23. The method of claim 21 further comprising demounting the reservoir component from the shield.

24. The method of claim 23 further comprising adding a buffer solution to the reservoir interior.

25. The method of claim 24 further comprising analyzing the oral fluids.

26. The method of claim 21 wherein the one reservoir component of the plurality of attachable reservoir components has disposed within the reservoir interior a buffer solution.

27. The method of claim 26 further comprising analyzing the oral fluids.

* * * * *